(12) United States Patent
Hamilton et al.

(10) Patent No.: US 6,896,842 B1
(45) Date of Patent: May 24, 2005

(54) MEDICAL DEVICE BALLOONS CONTAINING THERMOPLASTIC ELASTOMERS

(75) Inventors: Bruce Hamilton, Lowell, MA (US); Ronald A. Sahatjian, Lexington, MA (US)

(73) Assignee: Boston Scientific Corporation, Watertown, MA (US)

( * ) Notice: Subject to any disclaimer, the term of this patent is extended or adjusted under 35 U.S.C. 154(b) by 0 days.

(21) Appl. No.: 09/557,258

(22) Filed: Apr. 24, 2000

Related U.S. Application Data

(63) Continuation of application No. 09/129,029, filed on Aug. 4, 1998, now Pat. No. 6,086,556, which is a continuation of application No. 08/653,117, filed on May 24, 1996, now Pat. No. 5,797,877, which is a continuation of application No. 08/530,825, filed on Sep. 20, 1995, now abandoned, which is a continuation of application No. 08/364,431, filed on Dec. 27, 1994, now abandoned, which is a continuation of application No. 08/130,283, filed on Oct. 1, 1993, now abandoned.

(51) Int. Cl.[7] .............................................. B29D 23/00
(52) U.S. Cl. ....................................... 264/515; 264/573
(58) Field of Search ................................. 264/515, 573

(56) References Cited

U.S. PATENT DOCUMENTS

| | | |
|---|---|---|
| 1,643,289 A | 9/1927 | Peglay |
| 1,690,995 A | 11/1928 | Pratt |
| 2,499,045 A | 2/1950 | Walker et al. |
| 2,548,602 A | 4/1951 | Greenburg |
| 2,616,429 A | 11/1952 | Mereniender |
| 2,688,329 A | 9/1954 | Wallace |
| 2,690,595 A | 10/1954 | Raiche |
| 2,799,273 A | 7/1957 | Oddo |
| 2,823,421 A | 2/1958 | Scarlett |

(Continued)

FOREIGN PATENT DOCUMENTS

| | | |
|---|---|---|
| DE | 28 48 854 A1 | 5/1979 |
| DE | 36 38 828 A1 | 5/1988 |
| DE | 31 24 198 A1 | 4/1992 |
| DK | 130805 | 5/2002 |
| EP | 0 101 216 A2 | 2/1984 |
| EP | 0 166 998 | 1/1986 |
| EP | 0 174 206 A2 | 3/1986 |
| EP | 0 201 331 A2 | 11/1986 |
| EP | 0 214 721 A1 | 3/1987 |
| EP | 0 217 569 A2 | 4/1987 |

(Continued)

OTHER PUBLICATIONS

Patent Specification, (LaVeen), Patent No. 1,533,204.
Patent Specification, Patent No. 1,556,242.
Patent Specification, Serial No. 693,224.
Patent Specification, Patent No. 1,600,963.

(Continued)

*Primary Examiner*—Suzanne E. McDowell
(74) *Attorney, Agent, or Firm*—Fish & Richardson P.C.

(57) ABSTRACT

A dilatation balloon and catheter for insertion into a bodily conduit. The catheter (10) includes shaft (12) and a dilatation balloon (24) at the distal end of the shaft. The balloon is inflated via a central lumen (14) in the shaft for delivery of a fluid inflation media. The balloon is fabricated from a combination of a thermoplastic elastomer (TPE), preferably an engineering thermoplastic elastomer (ETE), with a non-compliant structural polymeric material. The combination may be a blend of the non-compliant structural polymer and the TPE. Alternatively, the combination may be a layered balloon having, for example, a non-compliant structural polymer inner layer and a soft, abrasion resistant, elastomeric outer layer. Methods for fabricating the balloon from the combination of a TPE and a non-compliant structural polymer are also disclosed.

13 Claims, 1 Drawing Sheet

U.S. PATENT DOCUMENTS

| | | |
|---|---|---|
| 2,936,760 A | 5/1960 | Gants |
| 2,981,254 A | 4/1961 | Vanderbilt |
| 3,045,677 A | 7/1962 | Wallace |
| 3,053,257 A | 9/1962 | Birtwell |
| 3,141,912 A | 7/1964 | Goldman et al. |
| 3,173,418 A | 3/1965 | Baran |
| 3,292,627 A | 12/1966 | Harautuneian |
| 3,304,353 A | 2/1967 | Harautuneian |
| 3,348,542 A | 10/1967 | Jackson |
| 3,426,744 A | 2/1969 | Ball |
| 3,432,591 A | 3/1969 | Heffelfinger |
| 3,539,674 A | 11/1970 | Dereniuk et al. |
| 3,543,758 A | 12/1970 | McWhorter |
| 3,543,759 A | 12/1970 | McWhorter |
| 3,561,493 A | 2/1971 | Maillard |
| 3,562,352 A | 2/1971 | Nyilas |
| 3,618,614 A | 11/1971 | Flynn |
| 3,707,146 A | 12/1972 | Cook et al. |
| 3,707,151 A | 12/1972 | Jackson |
| 3,731,692 A | 5/1973 | Goodyear |
| 3,733,309 A | 5/1973 | Wyeth et al. |
| 3,745,150 A | 7/1973 | Corsover |
| 3,769,984 A | 11/1973 | Muench |
| 3,799,172 A | 3/1974 | Szpur |
| 3,814,137 A | 6/1974 | Martinez |
| 3,833,004 A | 9/1974 | Vazquez et al. |
| 3,837,347 A | 9/1974 | Tower |
| 3,842,240 A | 10/1974 | Wakita et al. |
| 3,861,972 A | 1/1975 | Glover et al. |
| 3,888,852 A | 6/1975 | Wu et al. |
| 3,889,685 A | 6/1975 | Miller, Jr. et al. |
| 3,924,634 A | 12/1975 | Taylor et al. |
| 3,959,426 A | 5/1976 | Seefluth |
| 3,962,519 A | 6/1976 | Rusch et al. |
| 3,996,938 A | 12/1976 | Clark, III |
| 4,011,189 A | 3/1977 | Keil |
| 4,035,534 A | 7/1977 | Nyberg |
| 4,046,151 A | 9/1977 | Rose |
| 4,047,868 A | 9/1977 | Kudo et al. |
| 4,061,707 A | 12/1977 | Nohtomi et al. |
| 4,077,017 A | 2/1978 | Gilson et al. |
| 4,079,850 A | 3/1978 | Suzuki et al. |
| 4,085,757 A | 4/1978 | Pevsner |
| 4,105,022 A | 8/1978 | Antoshkiw et al. |
| 4,140,126 A | 2/1979 | Choudhury |
| 4,141,364 A | 2/1979 | Schultze |
| 4,144,298 A | 3/1979 | Lee |
| 4,174,783 A | 11/1979 | Abe et al. |
| 4,182,457 A | 1/1980 | Yamada et al. |
| 4,183,102 A | 1/1980 | Guiset |
| 4,195,637 A | 4/1980 | Gruntzig et al. |
| 4,198,981 A | 4/1980 | Sinnreich |
| 4,211,741 A | 7/1980 | Ostoich |
| 4,213,461 A | 7/1980 | Pevsner |
| 4,222,384 A | 9/1980 | Birtwell |
| 4,230,110 A | 10/1980 | Beroff |
| 4,233,022 A | 11/1980 | Brady et al. |
| 4,233,443 A | 11/1980 | Petropoulos et al. |
| 4,238,443 A | 12/1980 | Levy |
| 4,244,914 A | 1/1981 | Ranalli et al. |
| 4,251,564 A | 2/1981 | Cannella et al. |
| 4,256,789 A | 3/1981 | Suzuki et al. |
| 4,261,339 A | 4/1981 | Hanson et al. |
| 4,263,188 A | 4/1981 | Hampton et al. |
| 4,265,276 A | 5/1981 | Hatada et al. |
| 4,265,848 A | 5/1981 | Rusch |
| 4,271,839 A | 6/1981 | Fogarty et al. |
| 4,282,876 A | 8/1981 | Flynn |
| 4,292,974 A | 10/1981 | Fogarty et al. |
| 4,296,156 A | 10/1981 | Lustig et al. |
| 4,299,226 A | 11/1981 | Banka |
| 4,300,550 A | 11/1981 | Gandi et al. |
| 4,301,053 A | 11/1981 | Wolfrey |
| 4,306,998 A | 12/1981 | Wenzel et al. |
| 4,318,947 A | 3/1982 | Joung |
| 4,323,071 A | 4/1982 | Simpson et al. |
| 4,324,262 A | 4/1982 | Hall |
| 4,326,532 A | 4/1982 | Hammar |
| 4,327,736 A | 5/1982 | Inoue |
| 4,330,497 A | 5/1982 | Agdanowski |
| 4,335,723 A | 6/1982 | Patel |
| 4,338,942 A | 7/1982 | Fogarty |
| 4,346,698 A | 8/1982 | Hanson et al. |
| 4,351,341 A | 9/1982 | Goldberg et al. |
| 4,378,803 A | 4/1983 | Takagi et al. |
| 4,385,089 A | 5/1983 | Bonnebat et al. |
| 4,390,668 A | 6/1983 | Garver, Sr. |
| 4,403,612 A | 9/1983 | Fogarty |
| 4,406,656 A | 9/1983 | Hattler et al. |
| 4,409,364 A | 10/1983 | Schmukler et al. |
| 4,411,055 A | 10/1983 | Simpson et al. |
| 4,413,989 A | 11/1983 | Schjeldahl et al. |
| 4,417,576 A | 11/1983 | Baran |
| 4,422,447 A | 12/1983 | Schiff |
| 4,423,725 A | 1/1984 | Baran et al. |
| 4,423,829 A | 1/1984 | Katz |
| 4,424,242 A | 1/1984 | Barbee |
| 4,434,797 A | 3/1984 | Silander |
| 4,439,394 A | 3/1984 | Appleyard |
| 4,444,188 A | 4/1984 | Bazell et al. |
| 4,456,011 A | 6/1984 | Warnecke |
| 4,472,129 A | 9/1984 | Siard |
| 4,479,497 A | 10/1984 | Fogarty et al. |
| 4,484,971 A | 11/1984 | Wang |
| 4,490,421 A | 12/1984 | Levy |
| 4,497,074 A | 2/1985 | Rey et al. |
| 4,521,564 A | 6/1985 | Solomon et al. |
| 4,531,997 A | 7/1985 | Johnston |
| 4,540,404 A | 9/1985 | Wolvek |
| 4,551,292 A | 11/1985 | Fletcher et al. |
| 4,553,545 A | 11/1985 | Maass et al. |
| 4,559,951 A | 12/1985 | Dahl et al. |
| 4,563,181 A | 1/1986 | Wijayarathna et al. |
| 4,572,186 A | 2/1986 | Gould et al. |
| 4,573,470 A | 3/1986 | Samson et al. |
| 4,573,966 A | 3/1986 | Weikl et al. |
| 4,576,142 A | 3/1986 | Schiff |
| 4,576,772 A | 3/1986 | Carpenter |
| 4,578,024 A | 3/1986 | Sicka et al. |
| 4,579,879 A | 4/1986 | Flynn |
| 4,580,568 A | 4/1986 | Gianturco |
| 4,581,390 A | 4/1986 | Flynn |
| 4,582,762 A | 4/1986 | Onohara et al. |
| 4,585,000 A | 4/1986 | Hershenson |
| 4,596,563 A | 6/1986 | Pande |
| 4,606,347 A | 8/1986 | Fogarty et al. |
| 4,608,984 A | 9/1986 | Fogarty |
| 4,610,662 A | 9/1986 | Weikl et al. |
| 4,613,517 A | 9/1986 | Williams et al. |
| 4,614,188 A | 9/1986 | Bazell et al. |
| 4,627,436 A | 12/1986 | Leckrone |
| 4,627,844 A | 12/1986 | Schmitt |
| 4,634,615 A | 1/1987 | Versteegh et al. |
| 4,636,195 A | 1/1987 | Wolinsky |
| 4,636,346 A | 1/1987 | Gold et al. |
| 4,636,442 A | 1/1987 | Beavers et al. |
| 4,637,396 A | 1/1987 | Cook |
| 4,638,805 A | 1/1987 | Powell |
| 4,640,852 A | 2/1987 | Ossian |
| 4,642,267 A | 2/1987 | Creasy et al. |
| 4,648,871 A | 3/1987 | Jacob |

| | | | | | |
|---|---|---|---|---|---|
| 4,650,466 A | 3/1987 | Luther | 4,868,044 A | 9/1989 | Tanaka et al. |
| 4,651,721 A | 3/1987 | Mikulich et al. | 4,869,263 A | 9/1989 | Segal et al. |
| 4,655,745 A | 4/1987 | Corbett | 4,871,094 A | 10/1989 | Gall et al. |
| 4,655,771 A | 4/1987 | Wallsten | 4,878,495 A | 11/1989 | Grayzel |
| 4,656,070 A | 4/1987 | Nyberg et al. | 4,880,682 A | 11/1989 | Hazelton et al. |
| 4,656,094 A | 4/1987 | Kojima et al. | 4,886,062 A | 12/1989 | Wiktor |
| 4,657,024 A | 4/1987 | Coneys | 4,896,667 A | 1/1990 | Magnuson et al. |
| 4,660,560 A | 4/1987 | Klein | 4,896,669 A | 1/1990 | Bhate et al. |
| 4,664,657 A | 5/1987 | Williamitis et al. | 4,898,591 A | 2/1990 | Jang et al. |
| 4,666,437 A | 5/1987 | Lambert | 4,900,303 A | 2/1990 | Lemelson |
| 4,677,017 A | 6/1987 | DeAntonis et al. | 4,906,237 A | 3/1990 | Johansson et al. |
| 4,681,092 A | 7/1987 | Cho et al. | 4,906,241 A | 3/1990 | Noddin et al. |
| 4,681,564 A | 7/1987 | Landreneau | 4,906,244 A | 3/1990 | Pinchuk et al. |
| 4,684,363 A | 8/1987 | Ari et al. | 4,909,252 A | 3/1990 | Goldberger |
| 4,685,447 A | 8/1987 | Iversen et al. | 4,913,701 A | 4/1990 | Tower |
| 4,685,458 A | 8/1987 | Leckrone | 4,921,483 A | 5/1990 | Wijay et al. |
| 4,686,124 A | 8/1987 | Onohara et al. | 4,923,450 A | 5/1990 | Maeda et al. |
| 4,686,982 A | 8/1987 | Nash | 4,932,956 A | 6/1990 | Reddy et al. |
| 4,693,243 A | 9/1987 | Buras | 4,932,958 A | 6/1990 | Reddy et al. |
| 4,694,838 A | 9/1987 | Wijayarthna et al. | 4,933,178 A | 6/1990 | Capelli |
| 4,699,611 A | 10/1987 | Bowden | 4,934,999 A | 6/1990 | Bader |
| 4,702,252 A | 10/1987 | Brooks et al. | 4,938,676 A | 7/1990 | Jackowski et al. |
| 4,705,502 A | 11/1987 | Patel | 4,941,877 A | 7/1990 | Montano, Jr. |
| 4,705,517 A | 11/1987 | DiPesa, Jr. | 4,946,464 A | 8/1990 | Pevsner |
| 4,705,709 A | 11/1987 | Vailancourt | 4,950,227 A | 8/1990 | Savin et al. |
| 4,706,670 A | 11/1987 | Andersen et al. | 4,950,239 A | 8/1990 | Gahara et al. |
| 4,710,181 A | 12/1987 | Fuqua | 4,952,357 A | 8/1990 | Euteneuer |
| 4,723,936 A | 2/1988 | Buchbinder et al. | 4,954,126 A | 9/1990 | Wallsten |
| 4,729,914 A | 3/1988 | Kliment et al. | 4,960,410 A | 10/1990 | Pinchuk |
| 4,732,152 A | 3/1988 | Wallsten et al. | 4,963,306 A | 10/1990 | Weldon |
| 4,737,219 A | 4/1988 | Taller et al. | 4,963,313 A | 10/1990 | Noddin et al. |
| 4,739,013 A | 4/1988 | Pinchuk | 4,964,853 A | 10/1990 | Sugiyama et al. |
| 4,743,257 A | 5/1988 | Tormala et al. | 4,973,301 A | 11/1990 | Nissenkorn |
| 4,744,366 A | 5/1988 | Jang | 4,979,491 A | 12/1990 | DeMeritt |
| 4,751,924 A | 6/1988 | Hammerschmidt et al. | 4,986,830 A | 1/1991 | Owens et al. |
| 4,753,765 A | 6/1988 | Pande | 4,994,033 A | 2/1991 | Shockey et al. |
| 4,762,129 A | 8/1988 | Bonzel | 4,994,047 A | 2/1991 | Walker et al. |
| 4,762,130 A | 8/1988 | Fogarty et al. | 4,994,072 A | 2/1991 | Bhate et al. |
| 4,762,589 A | 8/1988 | Akiyama et al. | 4,995,868 A | 2/1991 | Brazier |
| 4,763,653 A | 8/1988 | Rockey | RE33,561 E | 3/1991 | Levy |
| 4,769,030 A | 9/1988 | Pinchuk | 5,000,734 A | 3/1991 | Boussignac et al. |
| 4,771,776 A | 9/1988 | Powell et al. | 5,002,531 A | 3/1991 | Bonzel |
| 4,771,778 A | 9/1988 | Mar | 5,002,556 A | 3/1991 | Ishida et al. |
| 4,775,371 A | 10/1988 | Mueller, Jr. | 5,006,119 A | 4/1991 | Acker et al. |
| 4,776,337 A | 10/1988 | Palmaz | 5,015,231 A | 5/1991 | Keith et al. |
| 4,786,556 A | 11/1988 | Hu et al. | 5,017,325 A | 5/1991 | Jackowski et al. |
| 4,787,388 A | 11/1988 | Hofmann | 5,026,607 A | 6/1991 | Kiezulas |
| 4,790,831 A | 12/1988 | Skribiski | 5,035,694 A | 7/1991 | Kasprzyk et al. |
| 4,795,458 A | 1/1989 | Regan | 5,037,392 A | 8/1991 | Hillstead |
| 4,796,629 A | 1/1989 | Grayzel | 5,041,089 A | 8/1991 | Mueller et al. |
| 4,800,882 A | 1/1989 | Gianturco | 5,041,100 A | 8/1991 | Rowland et al. |
| 4,801,297 A | 1/1989 | Mueller | 5,041,125 A | 8/1991 | Montano, Jr. |
| 4,803,035 A | 2/1989 | Kresge et al. | 5,041,129 A | 8/1991 | Hayhurst et al. |
| 4,810,543 A | 3/1989 | Gould et al. | 5,042,985 A | 8/1991 | Elliott et al. |
| 4,811,737 A | 3/1989 | Rydell | 5,049,132 A | 9/1991 | Shaffer et al. |
| 4,814,231 A | 3/1989 | Onohara et al. | 5,057,092 A | 10/1991 | Webster, Jr. |
| 4,816,339 A | 3/1989 | Tu et al. | 5,057,106 A | 10/1991 | Kasevich et al. |
| 4,818,592 A | 4/1989 | Ossian | 5,059,269 A | 10/1991 | Hu et al. |
| 4,819,751 A | 4/1989 | Shimada et al. | 5,061,424 A | 10/1991 | Karimi et al. |
| 4,820,349 A | 4/1989 | Saab | 5,071,406 A | 12/1991 | Jang |
| 4,821,722 A | 4/1989 | Miller et al. | 5,071,686 A | 12/1991 | Genske et al. |
| 4,824,436 A | 4/1989 | Wolinsky | 5,074,840 A | 12/1991 | Yoon |
| 4,824,618 A | 4/1989 | Strum et al. | 5,075,152 A | 12/1991 | Tsukuda et al. |
| 4,834,721 A | 5/1989 | Onohara et al. | 5,077,352 A | 12/1991 | Elton |
| 4,838,876 A | 6/1989 | Wong et al. | 5,084,315 A | 1/1992 | Karimi et al. |
| 4,840,623 A | 6/1989 | Quackenbush | 5,087,244 A | 2/1992 | Wolinsky et al. |
| 4,851,009 A | 7/1989 | Pinchuk | 5,087,246 A | 2/1992 | Smith |
| 4,856,516 A | 8/1989 | Hillstead | 5,090,958 A | 2/1992 | Sahota |
| 4,857,046 A | 8/1989 | Stevens et al. | 5,091,205 A | 2/1992 | Fan |
| 4,857,393 A | 8/1989 | Kato et al. | 5,094,799 A | 3/1992 | Takashige et al. |
| 4,863,426 A | 9/1989 | Ferragamo et al. | 5,100,381 A | 3/1992 | Burns |

| Patent Number | Date | Inventor |
|---|---|---|
| 5,100,721 A | 3/1992 | Akao |
| 5,100,992 A | 3/1992 | Cohn et al. |
| 5,102,416 A | 4/1992 | Rock |
| 5,108,415 A | 4/1992 | Pinchuk et al. |
| 5,108,420 A | 4/1992 | Marks |
| 5,114,423 A | 5/1992 | Kasprzyk et al. |
| 5,116,318 A | 5/1992 | Hillstead |
| 5,116,357 A | 5/1992 | Eberbach |
| 5,125,913 A | 6/1992 | Quackenbush |
| 5,137,512 A | 8/1992 | Burns et al. |
| 5,141,515 A | 8/1992 | Eberbach |
| 5,147,302 A | 9/1992 | Euteneuer et al. |
| 5,156,857 A | 10/1992 | Wang et al. |
| 5,160,321 A | 11/1992 | Sahota |
| 5,163,949 A | 11/1992 | Bonutti |
| 5,171,221 A | 12/1992 | Samson |
| 5,176,693 A | 1/1993 | Pannek, Jr. |
| 5,176,697 A | 1/1993 | Hasson et al. |
| 5,179,174 A | 1/1993 | Elton |
| 5,183,464 A | 2/1993 | Dubrul et al. |
| 5,183,613 A | 2/1993 | Edwards |
| 5,192,296 A | 3/1993 | Bhate et al. |
| 5,195,969 A | 3/1993 | Wang et al. |
| 5,195,970 A | 3/1993 | Gahara |
| 5,195,972 A | 3/1993 | Inoue |
| 5,201,706 A | 4/1993 | Noguchi et al. |
| 5,207,700 A | 5/1993 | Euteneuer |
| 5,209,728 A | 5/1993 | Kraus et al. |
| 5,213,576 A | 5/1993 | Abiuso et al. |
| 5,223,205 A | 6/1993 | Jackowski et al. |
| 5,224,933 A | 7/1993 | Bromander |
| 5,226,880 A | 7/1993 | Martin |
| 5,226,887 A | 7/1993 | Farr et al. |
| 5,248,305 A | 9/1993 | Zdrahala |
| 5,254,089 A | 10/1993 | Wang |
| 5,254,090 A | 10/1993 | Lombardi et al. |
| 5,254,091 A | 10/1993 | Aliahmad et al. |
| 5,256,421 A | 10/1993 | Casper |
| 5,263,962 A | 11/1993 | Johnson et al. |
| 5,264,260 A | 11/1993 | Saab |
| 5,266,899 A | 11/1993 | Bull et al. |
| 5,267,959 A | 12/1993 | Forman |
| 5,269,757 A | 12/1993 | Fagan et al. |
| 5,270,086 A | 12/1993 | Hamlin |
| 5,272,012 A | 12/1993 | Opolski |
| 5,277,199 A | 1/1994 | DuBois et al. |
| 5,279,560 A | 1/1994 | Morrill et al. |
| 5,279,594 A | 1/1994 | Jackson |
| 5,284,473 A | 2/1994 | Calabria |
| 5,290,306 A * | 3/1994 | Trotta et al. |
| 5,295,960 A | 3/1994 | Aliahmad et al. |
| 5,295,962 A | 3/1994 | Crocker et al. |
| 5,304,171 A | 4/1994 | Gregory et al. |
| 5,304,197 A | 4/1994 | Pinchuk et al. |
| 5,304,340 A | 4/1994 | Downey |
| 5,306,246 A | 4/1994 | Sahatjian et al. |
| 5,312,356 A | 5/1994 | Engelson et al. |
| 5,318,041 A | 6/1994 | DuBois et al. |
| 5,318,586 A | 6/1994 | Ereren |
| 5,318,587 A | 6/1994 | Davey |
| 5,328,468 A * | 7/1994 | Kaneko et al. ........ 604/103.13 |
| 5,330,428 A | 7/1994 | Wang et al. |
| 5,330,429 A | 7/1994 | Noguchi et al. |
| 5,334,146 A | 8/1994 | Ozasa |
| 5,334,168 A | 8/1994 | Hemmer |
| 5,338,298 A | 8/1994 | McIntyre |
| 5,342,301 A | 8/1994 | Saab |
| 5,342,305 A | 8/1994 | Shonk |
| 5,342,307 A | 8/1994 | Euteneuer et al. |
| 5,342,386 A | 8/1994 | Trotta |
| 5,344,400 A | 9/1994 | Kaneko et al. |
| 5,344,401 A | 9/1994 | Radisch et al. |
| 5,348,536 A | 9/1994 | Young et al. |
| 5,350,361 A | 9/1994 | Tsukashima et al. |
| 5,352,236 A | 10/1994 | Jung et al. |
| 5,358,486 A | 10/1994 | Saab |
| 5,360,401 A | 11/1994 | Turnland et al. |
| 5,366,442 A | 11/1994 | Wang et al. |
| 5,366,472 A | 11/1994 | Hillstead |
| 5,370,618 A | 12/1994 | Leonhardt |
| 5,372,603 A | 12/1994 | Acker et al. |
| 5,415,653 A | 5/1995 | Wardle et al. |
| 5,417,671 A | 5/1995 | Jackson |
| 5,423,773 A | 6/1995 | Jimenez |
| 5,447,497 A * | 9/1995 | Sogard et al. ......... 604/101.02 |
| 5,490,839 A | 2/1996 | Wang et al. |
| 5,526,823 A * | 6/1996 | Wheeler et al. |
| 5,554,120 A * | 9/1996 | Chen et al. |
| 5,556,383 A * | 9/1996 | Wang et al. |
| 5,587,125 A | 12/1996 | Roychowdhury |
| 5,613,979 A * | 3/1997 | Trotta et al. |
| 5,797,877 A * | 8/1998 | Hamilton et al. |
| 5,830,182 A * | 11/1998 | Wang et al. |
| 5,833,657 A * | 11/1998 | Reinhardt et al. |
| 5,871,468 A * | 2/1999 | Kramer et al. |
| 5,908,406 A * | 6/1999 | Ostapchenko et al. |
| 5,910,540 A * | 6/1999 | Takahashi |
| 6,086,556 A | 7/2000 | Hamilton et al. |
| 6,171,278 B1 | 1/2001 | Wang et al. |
| 6,358,227 B1 | 3/2002 | Ferrera et al. |
| 6,406,457 B1 | 6/2002 | Wang et al. |
| 6,416,494 B1 | 7/2002 | Wilkins |
| 6,585,688 B2 | 7/2003 | Ferrera et al. |
| 6,765,059 B2 | 7/2004 | Corley |
| 2002/0018866 A1 | 2/2002 | Lee et al. |
| 2002/0132072 A1 | 9/2002 | Wang et al. |
| 2003/0149468 A1 | 8/2003 | Wallsten |
| 2003/0167067 A1 | 9/2003 | Wang et al. |
| 2004/0019362 A1 | 1/2004 | Ferrera et al. |

FOREIGN PATENT DOCUMENTS

| | | |
|---|---|---|
| EP | 0 266 957 A2 | 5/1988 |
| EP | 0 274 411 | 7/1988 |
| EP | 0 276 908 A | 8/1988 |
| EP | 0 292 587 A1 | 11/1988 |
| EP | 0 303 487 A2 | 2/1989 |
| EP | 0 329 041 A2 | 8/1989 |
| EP | 0 357 562 | 3/1990 |
| EP | 0 358 445 A2 | 3/1990 |
| EP | 0 359 489 A2 | 3/1990 |
| EP | 0 414 350 B1 | 3/1990 |
| EP | 0 380 102 A1 | 8/1990 |
| EP | 0 383 429 | 8/1990 |
| EP | 0 399 712 A1 | 11/1990 |
| EP | 0 419 291 A1 | 3/1991 |
| EP | 0 420 488 A1 | 4/1991 |
| EP | 0 428 479 A1 | 5/1991 |
| EP | 0 439 202 A2 | 7/1991 |
| EP | 0 457 456 A1 | 11/1991 |
| EP | 0 461 474 A1 | 12/1991 |
| EP | 0 549 100 A1 | 6/1993 |
| EP | 0 553 960 A1 | 8/1993 |
| EP | 0 569 263 A2 | 11/1993 |
| EP | 0 636 382 A1 | 2/1995 |
| FR | 998035 | 1/1952 |
| FR | 2 328 482 | 5/1977 |
| GB | 2 077 111 A | 12/1981 |
| GB | 2 078 114 A | 1/1982 |
| GB | 2 130 093 | 5/1984 |
| GB | 2 140 437 A | 11/1984 |
| GB | 2 163 386 A | 2/1986 |
| GB | 2 209 121 A | 5/1989 |

| | | |
|---|---|---|
| JP | 50 75256 | 6/1975 |
| JP | 51 084877 | 7/1976 |
| JP | 53 042256 | 4/1978 |
| JP | 55 92743 | 7/1980 |
| JP | 58 38778 | 3/1983 |
| JP | 58 188463 | 11/1983 |
| JP | 59 167253 | 9/1984 |
| JP | 62 111734 | 5/1987 |
| JP | 63 12661 | 1/1988 |
| JP | 63 087219 | 4/1988 |
| JP | 1 132642 | 5/1989 |
| JP | 2 43036 | 2/1990 |
| JP | 3 277374 | 12/1991 |
| JP | 4 34590 | 2/1992 |
| JP | 4-144572 | 5/1992 |
| JP | 4 288232 | 10/1992 |
| JP | 5 305146 | 11/1993 |
| JP | 6 171043 | 8/1994 |
| SU | 069826 A | 1/1984 |
| SU | 1271523 A | 11/1986 |
| SU | 1477423 | 5/1989 |
| WO | WO 84/01327 | 4/1984 |
| WO | WO 91/04068 | 4/1991 |
| WO | WO 91/17788 | 11/1991 |
| WO | WO 92/08512 | 5/1992 |
| WO | WO 92/11893 | 7/1992 |
| WO | WO 92/19316 | 11/1992 |
| WO | WO 92/19440 | 11/1992 |
| WO | WO 93/15908 | 8/1993 |
| WO | WO 93/19800 | 10/1993 |
| WO | WO 93/21884 | 11/1993 |
| WO | WO 94/04216 | 3/1994 |
| WO | WO 94/27665 | 12/1994 |

OTHER PUBLICATIONS

Fisher et al., "Acute Aortic Dissection: Typical and Atypical Imaging Features", Scientific Exhibit, vol. 14, No. 6, pp. 1264–1271, 1994.

Lasch et al., "Intraesophageal Balloon Distention in the Evaluation of Sensory Thresholds: Studies on Reproducibility . . . Composition", American Journal Gastroenterology, vol. 89, No. 8, pp. 1185–1190, 1994.

Article Search—Woman's kin sues C.R. Bard over '88 death . . . Feb. 10, 1994, Boston Globe (MA), pp. 41.

Kiemeneij et al., "First Clinical Experience With a New Low Profile Coronary Perfusion . . . Guiding Catheters", The Journal of Invasive Surgery, vol. 5, No. 6, pp. 219–224, 1993.

Article Search, C.R. Bard, Inc., Company Report, PMT, Jan. 28, 1993, Investext pp. 1–8.

Matsumoto et al., "Peripheral Angioplasty Balloon Technology", Cardiovasc Intervent Radiol 16:135–143, 1993.

Article Search, Bard's "Inadequate" failure investigations for catheters prompt FDA warning letter, Apr. 27, 1992: MDDI Reports Gray Sheet.

Hermann et al., "Overview of Catheter–Based Therapy in Vascular Surgery", Current Surgery, vol. 48, No. 4, pp. 242–245, 1991.

Article from Design Ovine Hoestche Celen USC, 1991.

"Extruded Tubing is Called on to Perform More Complex and Critical Surgical Jobs", Modern Plastics International, pp. 40–41, 1990.

LeMay et al., "Pinhole Balloon Rupture During Coronary Angioplasty Causing Rupture of the Coronary Artery", Catheritation and Cardiovascular Diagnosis 19:91–92, 1990.

Johnson et al., "A Sexually Transmitted Diseases Cirriculum in Adolescent Medicine", American Journal of Diseases of Children, vol. 143, No. 7, pp. 1073–1076, 1989.

Davey, "Pleated Balloon Catheter", Biomedical Materials, 1989.

Chin et al., "Long–term Results of Intraoperative Balloon Dilatation", The Journal of Cardiovasular Surgery, 30:454–458, 1989.

Article from Plastics & Rubber Weekly, "Chemistry Advance Offers New Materials", p. 8, Dec. 3, 1988.

"New Silicone–modified TPE Combined Best of Both Worlds", Biomedical Elastomers, pp. 28–30, Nov. 1988.

Article from Plastic World, "New Tie Layers Brighten Life for Coextruders", 46n, Jul. 7, 1988.

"Film Laminate Key to Record Setting Balloon Flight", Plastics Design Forum, pp. 66–68, Mar./Apr. 1988.

Palmaz et al., "Intraluminal Stents in Atheroscierotic Iliac Artery Stenosis: Preliminary Report of a Multicenter Study", Radiology 168:727–731, 1988.

Mobley et al., "Effects of Organophosphorus Agents on Sarcoplasmic Reticulum in Skinned Skeletal Muscle Fibres", Toxicology and Applied Pharmacology, 94:407–413, 1988.

Carley, "A Plastics Primer", Modern Plastics Encyclopedia, pp. 4–8, 1988.

Shedd, Rader, Edenbaum et al., Willwerth et al., Gabbett, Peters, Tomanek et al., Clark, Modern Plastics Encyclopedia, pp. 93–109, 1988.

Woods, "Polyurethanes" and Torkelson "Silicones", Modern Plastics Encyclopdia, pp. 122–124, 1988.

Irwin, Belcher, Bruning and Suit, Modern Plastics Encyclopedia, pp. 203–210, 1988.

Reckner, "Testing by ASTM Methods", Modern Plastics Encyclopedia, pp. 318–320, 1988.

Wholey, "A Newly Designed Angioplasty Catheter: 'The Gemini Balloon'", CardioVascular and Interventional Radiology, 11:42–44, 1988.

"Surface Analysis of Biomedical Materials and Devices—Part 1", Biomedical Polymers, vol. 4, No. 7, pp. 1–15.

"In Vivo Assessment of Vascular Dilatation During Percutaneous Transluminal Coronary Angioplasty", American Journal of Cardiology, 60:968–982, Nov., 1987.

Articles from Plastics Technology, "Multi–Lumen Medical Tubing Line" and "Satellite Extruders for Coextrusion", 33 Aug. 1987.

M–D–D–I Reports, p. 15, Mar. 16, 1987.

Article from Elastomerics, 118 Nov. 1986, EuroNews by Maurice Botwell, "DuPont Uses New Design Concepts To Boost TP Elastomers In Europe".

Rees et al., "Recent Subsegmental Splenic Infarction: Hypervascular Appearace on Angiography", Journal of Vascular Disorders, vol. 37, No. 11, p. 793, Nov. 1986.

Levy, "Improved Dilation Catheter Balloons", Journal of Clinical Energy, pp. 291–296, Jul./Aug. 1986.

Article from Plastics and Rubber International, "Medical Uses Of Polymers", vol. 11, No. 3, Jun. 1986.

Jain et al., "Effect of Inflation Pressures on Coronary Angioplasty Balloons", American Journal of Cardiology, 57:26–28, Jan. 1, 1986.

Palmaz et al., "Expandable Intrahepatic Portacaval Shunt Stents: Early Experience in the Dog", AJR 145:821–825, Oct. 1985.

Palmaz et al., "Expandable Intraluminal Graft: A Preliminary Study", Radiology, vol. 156 No. 1, Jul. 1985.

Inoue, "A New Balloon Catheter for Percutaneous Transluminal Angioplasty", AJR 144:1069–1071, May 1985.

Giesy et al., "Coaxial and Linear Extrusion Balloon Catheters Compared to Guidewires . . . Urinary Tract", The Journal of Urology, vol. 133, No. 4, p. 238A, Apr. 1985.

Videotape presentation of Oct. 21, 1988 given by John E. Abele at the Texas Heart Institute in Houston, Texas (previously submitted to PTO Aug. 26, 1996).

Letter from Modern Plastics, "Coextrusion Measurement by IR Sensors", Jun. 1984 14:8.

Kinney et al., "Shear Force in Angioplasty: Its Relation to Catheter Design and Function", American Journal of Roentgenology, 144:115–122, Jan. 1985.

Giesy et al., Ureteral Access: Bypassing Impacted Stones . . . Balloon Catheter, The Journal of Urology, vol. 131, No. 4, 152A, 79th Annual Meeting of American Urological Association, Inc., May 6–10, 1984.

Giesy et al., "Coaxial Balloon Dilation and Calibration of Urethral Strictures", The American Journal of Surgery, 147:611–614, May 1984.

Fogarty et al., "Current Status of Dilatation Catheters and Guiding Systems", The American Journal of Cardiology, vol. 53, No. 8, pp. 97C–100C, Apr. 1, 1984.

Inoue et al., "Clinical Application of Transvenous Mitral Commissurotomy by a New Balloon Catheter", Journal of Thoracic and Cardiovascular Surgery, vol. 87, No. 3, pp. 394–402, Mar. 1984.

Kennedy et al., "Interventional Coronary Arteriography", Annual Review of Medicing: Selected Topics in the Clinical Sciences, 35:513–516, 1984.

Broad, "Plastics Revolution: A Rush of New Uses",The New York Times, Tuesday, Nov. 1, 1983.

"The Gamma Bottle", Food & Drug Packaging, vol. 47, No. 10, Oct. 1983.

"Award Caps Bottle's Introduction", USA Today, Friday, Oct. 7, 1983.

Forcinio, "Squeezable bottle ends long wait for ketchup", Food & Drug Packaging, vol. 4, No. 10, Oct. 1983.

"Rigid Plastics Are Getting a Foot in the Kitchen Door", Chemical Week, Oct. 12, 1983.

Kent et al., "Percutaneous Transluminal Coronary Angioplasty: Report From . . . Blood Institute", The American Journal of Cardiology, vol. 49, pp. 2011–2020, Jun. 1982.

Dobrin, "Balloon Embolectomy Catheters in Small Arteris, I Lateral Wall Pressures and Shear Forces", Surgery, vol. 90, No. 2, pp. 177–185, Aug. 1981.

Modern Plastics Encyclopedia 1988, vol. 64, No. 10A, pp. 93–100 (Oct. 1987).

Modern Plastics Encyclopedia 1990, vol. 66, No. 11, pp. 122–131 (Mid–Oct. 1989).

Forgarty et al., "Adjunctive Intraoperative Arterial Dilation", Arch. Surg., 116:1381–1397, 1981.

Jekell et al., "Balloon Catheters", Acta Radiological Diagnosis, 21:47–52, 1980.

Katzen et al., "Percutaneous Transluminal Angioplasty With the Gruntzig Balloon Catheter", Arch Surg., vol. 114, No. 12, pp. 1389–1399, Jun. 1979.

Gruntzzig et al., "Technique of Percutaneous Transluminal Anoplasty with the Gruntzig Balloon Catheter", American Journal of Roentgenology, vol. 132, No. 4, pp. 547–552, Apr. 1979.

Jensen, "Double–Lumen Balloon Catheter", Acta Radiological Diagnosis, 17:886–890, Nov. 1976.

Supplements to Circulation, An Official Journal of the American Heart Association, vols. 53 and 54, p. II–81, Jan.–Dec. 1976.

Radiology, vol. 115, No. 3, Jun. 1975.

Sweeting et al., "Auxiliary Film Treatments"& "Polyethylene Terephthalate Film Structure and Analysis", The Science and Technology of Polymer Films, vol. II John Wiley & Sons, Inc., pp. 619–633.

Adrova et al., "Polymides: A new Class of Heat–Resistant Polymers", Academy of Sciences of the USSR, Chapter 1, "Synthesis and Transformations of Polymides", pp. 1–36.

Fogarty, "The Balloon Catheter in Vascular Surgery", Review of Surgery, vol. 24, No. 1, pp. 9–19.

Encyclopedia of Polymer Science and Engineering, vol. 2, Biaxial Orientation, pp. 339–373.

Encyclopedia of Polymer Science and Engineering, vol. 2, Anionic Polymerization to Cationic Polymerization, p. 202; vol. 10, Molecular Weight . . . Polymers, pp. 619–636.

Abele, "Balloon Engineering and Materials", Coronary Balloon Angioplasty Recent Developments.

Adams, "PTCA Balloon Materials, Their Characteristics and Impact on Catheter Selection", Technical Notes SciMed Life Systems, Inc.

Paul, Polymer Blends, vol. 2, pp. 129–65, 1978.

* cited by examiner

FIG. 1
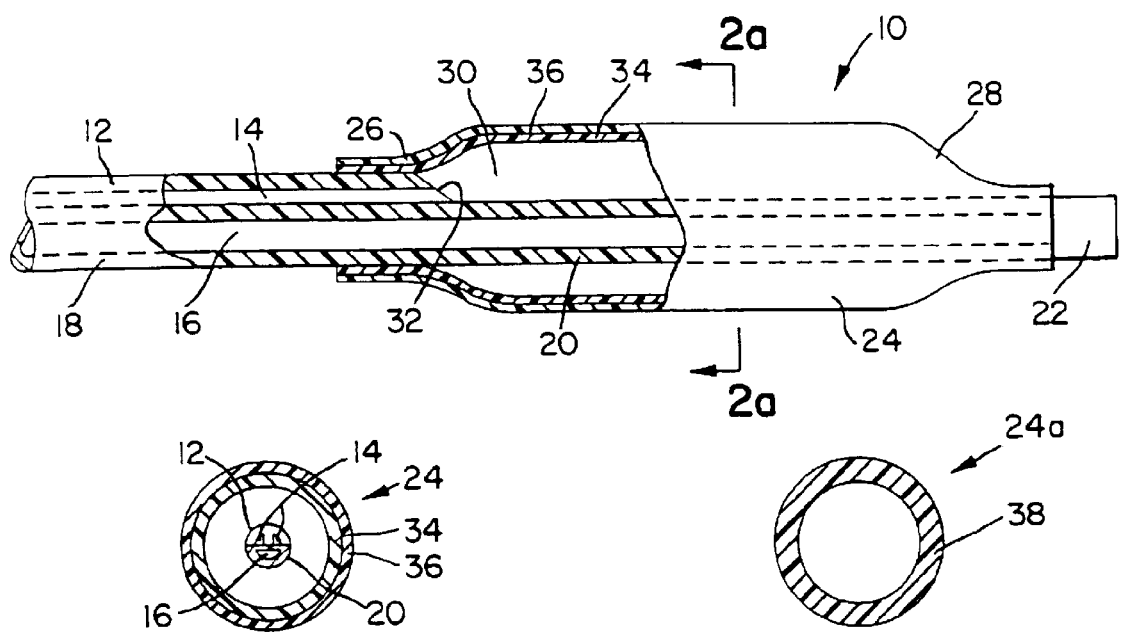
FIG. 2a
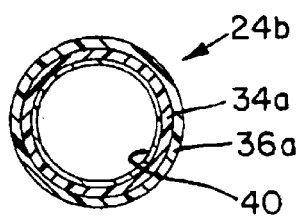
FIG. 2b
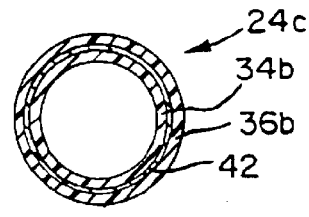
FIG. 2c
FIG. 2d

MEDICAL DEVICE BALLOONS CONTAINING THERMOPLASTIC ELASTOMERS

CROSS-REFERENCED TO RELATED APPLICATIONS

This application is a continuation of, and claims priority under 35 U.S.C. § 120 to, U.S. patent application Ser. No. 09/129,029, filed Aug. 4, 1998, now U.S. Pat. No. 6,086, 556, which is a continuation of U.S. patent application Ser. No. 08/653,117, filed May 24, 1996, now U.S. Pat. No. 5,797,877, which is a continuation of U.S. patent application Ser. No. 08/530,825, filed on Sep. 20, 1995, now abandoned, which is a continuation of U.S. patent application Ser. No. 08/364,431, filed on Dec. 27, 1994, now abandoned, which is a continuation of U.S. patent application Ser. No. 08/130, 283, filed on Oct. 1, 1993, now abandoned.

BACKGROUND OF THE INVENTION

The present invention relates to catheters that can be placed in bodily conduits. The invention particularly relates to dilatation balloons and catheters using such balloons for administering treatments to widen constricted passages in, for example, angioplasty, valvuloplasty, or urological procedures.

One example of such a procedure, angioplasty, is used to treat a stenosis, i.e. to restore adequate blood flow to a region of a blood vessel which has been narrowed to such a degree that blood flow is restricted. Frequently the stenosis can be expanded so that the vessel will permit an acceptable blood flow rate. Coronary angioplasty, for example, includes the insertion of a balloon catheter through a patient's coronary artery to an arterial stenosis and injecting a suitable fluid into the balloon to inflate it, hence expanding the stenosis radially outwardly. Angioplasty has proven to be a successful alternative to coronary arterial bypass surgery.

Typically, balloon catheters have a balloon fastened at at least one end around the exterior of a hollow catheter shaft. The hollow interior of the balloon is in fluid flow relation with the hollow interior of the shaft. The shaft then may be used to provide a fluid supply for inflating the balloon.

Presently used catheter balloons may be classified as compliant or non-compliant balloons. Compliant balloons expand and stretch with increasing pressure within the balloon, and are made from such materials as polyethylene or polyolefin copolymers. Non-compliant balloons, made from such materials as polyethylene terephthalate (PET) or polyamides, remain at a preselected diameter as the internal balloon pressure increases beyond that required to fully inflate the balloon.

Compliant balloon materials provide a degree of softness to the balloon which aids its passage through, e.g., blood vessels with minimal trauma. Known compliant balloon materials also can display good abrasion and puncture resistance at thicknesses typically used for medical device balloons. However, as mentioned above, they do not remain at the desired diameter with increasing pressure. Such compliant balloons also lack sufficient hoop strength to achieve high dilating forces.

A non-compliant balloon, that is one remaining at a preselected diameter regardless of increasing pressure, is often desirable. Typical non-compliant balloon materials do not exhibit the same degrees of softness and abrasion resistance as the compliant balloons.

It would be desirable, for many treatment conditions, to have a dilatation balloon exhibiting the combined characteristics of softness, abrasion and puncture resistance, hoop strength, and the ability to maintain a preselected diameter as the internal pressure within the balloon is increased. The balloon described herein was developed to address that need.

SUMMARY OF THE INVENTION

In one embodiment, the invention is a dilatation balloon for use in a medical catheter device. The dilatation balloon includes a thermoplastic elastomer in combination with a non-compliant structural polymeric material. The preferred thermoplastic elastomer includes an engineering thermoplastic elastomer, for example a polyether glycollpolybutylene terephthalate block copolymer. The thermoplastic elastomer may be combined with the non-compliant structural polymeric material as an outer elastomeric layer disposed upon an inner structural layer of the non-compliant structural polymeric material, as both an inner elastomeric layer and an outer elastomeric layer disposed upon an intermediate structural layer of the non-compliant structural polymeric material, or as a blend of the thermoplastic elastomer and the non-compliant structural polymeric material.

In another embodiment, the invention is a catheter for insertion into a bodily conduit. The catheter includes a shaft having a lumen internal to the shaft for delivery of fluid inflation media, and a dilatation balloon bonded to the shaft and defining a chamber. The chamber is in fluid communication with the lumen to permit inflation of the chamber. The dilatation balloon includes a thermoplastic elastomer in combination with a non-compliant structural polymeric material, as described above with respect to the balloon in accordance with the invention.

In yet another embodiment, the invention is a method for fabricating a dilatation balloon for use in a medical catheter device. The method involves producing a generally cylindrical balloon blank from a combination of a thermoplastic elastomer and a non-compliant structural material, and shaping the balloon blank to produce the dilatation balloon.

The balloon blank may be produced by disposing an elastomeric layer including the thermoplastic elastomer upon a structural layer including the non-compliant structural polymeric material to produce a layered, generally cylindrical balloon blank. The thermoplastic elastomer and the non-compliant structural polymeric material may be coextruded to produce the balloon blank. Alternatively, the balloon blank may be produced by preparing a blend of the therm plastic elastomer and the non-compliant structural polymeric material. A generally cylindrical balloon blank is formed from the blend, and the balloon blank is then shaped to produce the dilatation balloon. The balloon blank may be shaped to have a generally cylindrical central portion and generally conical end portions.

BRIEF DESCRIPTION OF THE DRAWINGS

For a better understanding of the present invention, together with other objects, advantages, and capabilities thereof, reference is made to the following Description and appended claims, together with the Drawings in which:

FIG. 1 is an elevation view of a medical balloon catheter, partly in section, in accordance with one embodiment of the present invention;

FIG. 2a is a cross-sectional view of the balloon of FIG. 1, taken along line 2a—2a, showing the balloon layers;

FIGS. 2b, 2c, and 2d are cross-sectional views similar to that shown in FIG. 2a (omitting the shaft distal end) illus-

DETAILED DESCRIPTION OF THE PREFERRED EMBODIMENTS

An exemplary embodiment of the balloon and catheter in accordance with the invention is described herein. The angioplasty catheter includes a balloon mounted at the distal end of a shaft including at least one lumen for inflation of the balloon. The balloon is a generally tubular body fabricated from a combination of a non-compliant structural polymeric material and a thermoplastic elastomer (TPE). The combination may be in the form of coextensive coextruded layers, otherwise disposed layers, blends, or blended layers of these materials. Once th catheter is in position within the patient's artery, a fluid inflation medium may be introduced via the lumen to inflate the balloon to the preselected desired diameter.

The term "structural polymer" or "structural polymeric material", as used herein, is intended to mean any polymeric material suitable for use in medical balloons and compatible with the TPE selected. As mentioned above, the term "noncompliant", as used herein, is intended to mean remaining at a preselected diameter as the internal pressure in the balloon is increased above that required to fully inflate the balloon. The structural layer of the balloon must be self supporting and capable of supporting at least one TPE layer thereon. Suitable non-compliant structural polymeric materials include, for example, modified polyesters, polyethylene terephthalate (PET), modified polybutylenes, polyvinyl chlorides, polyamides (e.g. Nylon), etc., or a combination thereof. Preferred are biaxially oriented non-compliant structural materials; most preferred is biaxially oriented PET.

The term "thermoplastic elastomer" or "TPE", as used herein, is intended to mean a polymeric material that combines the mechanical properties of a thermoset rubber, i.e. resiliency, softness, and toughness, with the production economics of a thermoplastic polymer. The TPEs include styrenic block copolymers, polyolefin blends (TPOs), elastomeric alloys, thermoplastic polyurethanes (TPUs), thermoplastic copolyesters, and thermoplastic polyamides. These materials have varying patterns of hard and soft segments included in the polymer chain or compound. The hard segments melt or soften at processing temperatures, producing a melt processable material for ease of fabrication. In block copolymer TPEs, the hard and soft regions are in the same polymer chain. Descriptions of various types of TPEs may be found in *Modern Plastics Encyclopedia* 1988, Vol. 64, No. 10A, pp. 93–100 (October 1987), and in *Modern Plastics Encyclopedia* 1990, Vol. 66, No. 11, pp. 122–131 (Mid-October 1989), both incorporated herein by reference.

The preferred TPEs for the balloon described herein are engineering thermoplastic elastomers (ETEs), which are randomized block copolymers having polyester crystalline hard segments and amorphous glycol soft segments. ETEs possess flexibility over a useful range of strain, and are quite extensible when operating within their elastic limit. Another advantage of ETEs for medical devices is their resistance to most radiation, permitting sterilization by such means, although they must be protected from UV radiation.

The more preferred ETEs for use in the medical devices described herein are randomized block copolymers of polyether glycol and polybutylene terephthalate (PBT).

These combine crystalline PBT hard segments with melt stable glycol soft segments, and come in a wide range of stiffness grades. Most preferred are those having a flexural modulus of about 21,000–440,000 psi (as measured in accordance with ASTM D790, Method 1), for example Hytrel® polymers (available from E.I. DuPont de Nemours and Company, Wilmington, Del.).

As mentioned above, the combination of a TPE and a non-compliant structural polymer may be in the form of blends, coextensive coextruded layers, otherwise disposed layers, or layers of blends of these materials. Suitable blends include homogeneous and near-homogeneous blends, which may be prepared by such conventional means as stirring, mixing, compounding, etc.

In a layered embodiment of the balloon, one or more base structural polymer layers are formed, for example by extrusion, from a non-compliant structural polymer, as described above. Alternatively, the bass non-compliant structural layer is formed from a blend of two or more structural polymers, a blend of a structural polymer with a minor amount of another polymeric material, or a blend of a structural polymer with a minor amount of a TPE. As used herein, the term "minor amount" is intended to mean an amount selected to make the additive no more than a secondary component, for example less than 50 weight %, of the blend. The material of the structural layer, however, must still contribute to the balloon the properties described above for the structural material. This base structural layer (or layers) is typically at least about 0.2–1.5 mil thick, and gives the balloon its tensile strength so that the balloon wall is self supporting.

At least one additional, elastomeric outer layer about 0.2–0.5 mil thick is coextruded with or otherwise disposed on the base layer and, typically, generally coextensive therewith. Normally, the elastomeric layer is significantly thinner than the structural layer. The material of this outer layer is based on a thermoplastic elastomer (TPE) which, in some embodiments, may be combined in a blend with other polymers known to be suitable for medical balloons. The amount of these other polymers, however, should be within limits which would permit such a blend to contribute to the balloon the properties described herein for such an elastomeric layer. Especially preferred for this outer elastomeric layer is a blend of an ETE with a small amount of a non-compliant structural polymer, e.g. a blend of about 1–10 weight % PET, remainder Hytrel elastomer.

In some of the above-described layered balloons, it may be advantageous to dispose or coextrude an adhesive or other polymer layer between two or more of the layers. In one embodiment, an adhesive layer may be included to improve adhesion between coextensive balloon layers and, if d sired, may be applied for adhesion of the medical device balloon to a catheter shaft. In another embodiment, an additional polymer layer may be included to contribute other desirable properties to the balloon, for example to contribute further to the softness and/or foldability of the balloon. In other embodiments, the adhesive or other polymer may be blended with a structural and/or elastomeric layer to contribute its properties to the balloon. For example, in a three layer balloon an adhesive polymer may be blended with a structural polymer layer to improve adhesion of inner and outer ETE layers to the structural layer. The amount of adhesive or other polymer in such a blend is selected to provide the desired enhancement of properties while permitting the blend to possess the properties described herein for such a lay r. Examples of adhesive materials for forming this layer or blend are Bynel® adhesive resin (E.I. DuPont de Nemours and Company, Wilmington, Del.) or Plexar® adhesive resin (Quantum Chemical Corp., Cincinnati, Ohio ). Selar® modified PET resin (E.I. DuPont de Nemours and Company, Wilmington, Del.) is a suitable polymer intermediate layer or blend additive for improving softness and foldability of the balloon. Bynel and Plexar resins can also serve to improve the abrasion resistance and puncture resistance of the balloon, and provide it with a softer feel.

In another embodiment of the balloon, a single layer balloon wall is fabricated from a blend of a non-compliant structural polymer and a TPE. The TPE, preferably the above-described polyether glycol/PBT block copolymer, is blended with the structural polymer in a TPE-to-structural polymer ratio selected to provide the desired degree of softness and abrasion resistance to the balloon without unduly compromising the hoop strength or the desired inflated diameter. As mentioned above, such blends may be homogeneous or near-homogeneous, and may be blended in any of several ways known in the art. Typical polymer ratios for such a single layer balloon are about 40:60 to 60:40, TPE:structural polymer.

In other embodiments, the TPE/structural polymer blend used in the above-described single layer balloon may be used as a structural layer in combination with other layers, or may be blended to be used as an elastomeric layer in a layered balloon. The polymer ratio for a blended structural layer of such a balloon is typically about 40:60 to 60:40, TPE:structural polymer; that for elastomeric inner or outer layers is typically about 30:70 to 60:40, TPE:structural polymer. The exact ratios within these ranges to produce specific balloon characteristics are empirically determined with minimal experimentation. These blended layers may be used with or without an adhesive or softening component or layer as described above The use of thermoplastic elastomers in medical device balloons results in a superior balance of balloon properties when used as one or more outer layers over a structural layer of currently used balloon materials or other suitable structural polymers, or as outer and inner layers surrounding such a structural layer. Alternatively, this superior balance of balloon properties may be achieved by using TPEs as a blend with currently used balloon materials or other suitable structural polymers. By varying the fabrication method and/or layer materials and/or blend materials and ratios, as described herein, the structural and surface properties of the ETE containing balloon may be precisely tailored for a desired procedure.

The description below of various illustrative embodiments shown in the Drawings refers to engineering thermoplastic elastomers (ETEs). However, it is not intended to limit the scope of the present inv ntion, but merely to b illustrative and representative thereof.

Referring now to FIG. 1, catheter 10 in accordance with one embodiment of the present invention includes shaft 12 having lumens 14 and 16 extending therethrough, and having a proximal end 18 and a distal end 20. Distal end 20 extends to catheter tip 22. Dilatation balloon 24, shown in FIG. 1 in its inflated state, surrounds shaft distal end 20. Balloon proximal end 26 is bonded to shaft distal end 20 at a point spaced from tip 22, and balloon distal end 28 is bonded to shaft distal end 20 near tip 22, each, e.g., by a suitable adhesive (not shown). Balloon 24 defines balloon chamber 30 which is in fluid communication with lumen 14 via aperture 32. Thus, balloon 24 may be inflated by passing a fluid inflation medium through lum n 14 and aperture 32 into chamber 30. Lumen 16 may be used, for example, to contain a guidewire or other device.

As shown in FIGS. 1 and 2a, dilatation balloon 24 surrounding shaft distal end 20 is made up of two layers, 34 and 36, of differing polymeric materials. Inner layer 34 is a structural layer of, e.g., PET approximately 0.2–1.0 mil thick. Outer layer 36 has been co-extruded to be coextensive with layer 34, and is a layer of ETE, e.g. Hytrel copolymer, about 0.2–0.5 mil thick.

FIGS. 2b, 2c, and 2d each illustrate alternate embodiments of the balloon of the invention in cross-section, similarly to FIG. 2a. For simplicity, however, shaft distal end 20, although actually present in the same position as shown in FIG. 2a, is not depicted in the view shown in FIGS. 2b–2d.

FIG. 2b illustrates in cross-section dilatation balloon 24a, fabricated from single layer 38 of a blend of a structural polymer, e.g. polyethylene terephthalate, with an ETE, for example Hytrel copolymer.

FIG. 2c shows balloon 24b fabricated from, e.g., coextruded triple layers, 34a, 36a, and 40. Structural layer 34a and ETE outer layer 36a are similar to layers 34 and 36 of FIGS. 1 and 2a. In the embodiment illustrated in FIG. 2c, however, an additional ETE layer, innermost layer 40, has been coextruded to be coextensive with layers 34a and 36a and internal thereto. Innermost layer 40 provides additional tear resistance to protect the balloon wall from damage from internal pressure. Layer 40 also provides for a softer, more foldable balloon.

FIG. 2d illustrates balloon 24c, fabricated in a similar manner to balloon 24 of FIGS. 1 and 2a, and having inner structural layer 34b and ETE outer layer 36b. Thin intermediate adhesive layer 42 of, e.g., Bynel resin is coextruded with and between layers 34b and 36b to be coextensive therewith, acting to bond together more securely layers 34b and 36b.

In other alternate embodiments, one or more of layers 34, 34a, and 34b may be a blend of a structural polymer with an ETE. Also alternatively, one or more of layers 36, 36a, 36b, or 40 may be a blend of ETE with a structural polymeric material. In the embodiment of FIG. 2c, a sufficient amount of a polymeric adhesive to improve bonding of the layers may be blended into layer 34a. Alternatively, layer 34a may be , e.g., a Selar resin balloon softening layer. Also alternatively, the adhesive or other polymeric additive may be blended into, e.g., layer 34, 36, 36a, 40, etc., as described above. In other alternate embodiments, not shown, the balloon may have more than one innermost and/or outermost ETE layer. For example, a balloon may be similar to that shown in FIG. 2a but have an additional ETE layer between layers 34 and 36, or may be similar to that shown in FIG. 2c but have an additional ETE layer between layers 34a and one or both of layers 36a and 40.

In operation, the catheter device including the novel dilatation balloon is inserted into the vasculature of a patient, and is manipulated into position by torquing, pushing, and pulling. Positioning of the catheter is aided by the softness of the balloon provided by the TPE component of the balloon. Once the catheter is in position, the balloon is inflated to the preselected diameter, then deflated via the central lumen of the shaft. The inclusion of a non-compliant structural polymer in the balloon makes possible such preselection of the diameter. Upon completion of the dilation procedure and deflation of the balloon, the catheter is removed from the patient. Removal of the catheter is also aided by the softness contributed to the balloon by the TPE component.

The invention described herein presents to the art novel, improved catheters and composite medical device balloons including thermoplastic elastomers as (a) one or more layers in addition to one or more layers of currently used balloon structural materials or other suitable structural polymers, or (b) as a blend with such materials. The inclusion of TPE results in a superior balance of balloon properties. For example, softer feel; superior abrasion and puncture resistance; lower required insertion, placement, and withdrawal forces; lower balloon resistance to inflation and deflation pressure; superior refoldability, with fold memory; and the ability to maintain a preselected diameter are all achievable in a single balloon fabricated as described herein. Thus, the balloon described herein can provide a non-compliant balloon with the softness of a compliant balloon, as well as a soft balloon with ranges of burst strength and hoop strength equivalent to those of harder balloons. The use of the adhesives and other layers or layer additives described herein, especially the Bynel and Plexar adhesives and Selar additive described, can offer advantageous adhesive and/or softening properties. By varying the fabrication method and/or layer or blend materials and ratios as described herein, the balance of structural and surface properties of the TPE containing balloon may be precisely tailored for a specific procedure.

While there has been shown and described what are at present considered the preferred embodiments of the invention, it will be apparent to those skilled in the art that modifications and changes can be made therein without departing from the scope of the present invention as defined by the appended claims.

We claim:

1. A method for fabricating a dilatation balloon for use in a medical catheter device, said method comprising the steps of:

producing a generally cylindrical balloon blank from a combination of a thermoplastic elastomer and a non-compliant structural material; and shaping said balloon blank to produce said dilatation balloon.

2. A method in accordance with claim 1 wherein said balloon blank producing step comprises disposing an elastomeric layer comprising said thermoplastic elastomer upon a structural layer comprising said non-compliant structural polymeric material to produce a layered, generally cylindrical balloon blank.

3. A method in accordance with claim 2 wherein said disposing step comprises coextruding said thermoplastic elastomer and said non-compliant structural polymeric material.

4. A method in accordance with claim 2 wherein said disposing step comprises disposing said structural layer as an inner layer and disposing said thermoplastic elastomer as an outer elastomeric layer on said inner structural layer.

5. A method in accordance with claim 2 wherein said disposing step comprises disposing said structural layer as an intermediate layer and disposing said thermoplastic elastomer as both an outer and an inner elastomeric layer on said intermediate structural layer.

6. A method in accordance with claim 1 wherein said disposing step producing step comprises: preparing a blend of a thermoplastic elastomer and a non-compliant structural polymeric material; and forming a generally cylindrical balloon blank from said blend.

7. A method in accordance with claim 1 wherein said shaping step comprises shaping said balloon blank such that said dilatation balloon has a generally cylindrical central portion and generally conical end portions.

8. The method of claim 1, wherein the thermoplastic elastomer is selected from the group consisting of styrenic block copolymers, polyolefin blends, elastomeric alloys, thermoplastic polyurethanes, thermoplastic copolyesters, and thermoplastic polyamides.

9. The method of claim 1, wherein the thermoplastic elastomer is an engineering thermoplastic elastomer.

10. The method of claim 1, wherein the thermoplastic elastomer is a polyether glycol/polybutylene terephthalate block copolymer.

11. The method of claim 1, wherein the non-compliant structural material is selected from the group consisting of modified polyesters, polyethylene terephthalate, modified polybutylenes, polyvinyl chlorides, polyamides, and combinations thereof.

12. The method of claim 1, wherein the non-compliant structural material is biaxially oriented.

13. The method of claim 1, wherein the non-compliant structural material is biaxially oriented polyethylene terephthalate.

* * * * *

UNITED STATES PATENT AND TRADEMARK OFFICE
CERTIFICATE OF CORRECTION

PATENT NO.         : 6,896,842 B1                                                Page 1 of 3
APPLICATION NO.    : 09/557258
DATED              : May 24, 2005
INVENTOR(S)        : Bruce Hamilton and Ronald A. Sahatjian It is certified that error appears in the above-identified patent and that said Letters Patent is hereby corrected as shown below:

On the cover page, under "U.S. Patent Documents", next to "2,616,429":

Replace "Mereniender" with --Merenlender--

On page 3:

Next to "4,706,670", replace "11/1987" with --11/1989--

Next to "4,995,868", replace "2/1991" with --3/1991--

Next to "5,041,089", replace "Mueller et al." with --Muelier et al.--

On page 4:

Next to 5,360,401, after "Turnland", delete "et al."

Under Foreign Patent Documents, replace "0 276 908 A" with "0 276 908 A1"

On page 5:

Under "Other Publications", for the "LeMay et al." publication, replace "Catheritation" with --Catherization--

Under "Other Publications", for the "Palmaz et al." publication, replace "Atheroscierotic" with --Atherosclerotic--

On page 6:

For the "Kennedy et al." publication, replace "Medicing" with --Medicine--

For the "Gruntzzig et al." publication, replace "Gruntzzig" with --Gruntzig--

At column 1, line 8:

Delete "Ser."

At column 1, line 10:

Delete "Ser."

At column 1, line 13:

Delete "Ser."

At column 1, line 14:

Delete "Ser."

At column 1, line 16:

Delete "Ser."

At column 2, line 13:

Replace "glycollpolybutylene" with --glycol/polybutylene--

At column 2, line 48:

Replace "therm plastic" with --thermoplastic--

At column 3, line 14:

Replace "th" with --the--

At column 4, line 50:

Replace "d sired" with --desired--

At column 4, line 64:

Replace "lay r" with --layer--

At column 5, line 31:

After "above", insert --.--

At column 5, line 49:

Replace "inv ntion" with --invention--

Replace "b" with --be--

CERTIFICATE OF CORRECTION (continued)
U.S. Pat. No. 6,896,842 B1

At column 5, line 63:

Replace "lum n" with --lumen--

At column 6, line 41:

Replace "be , e.g." with --be, e.g.--

At column 6, line 42:

Replace "alternatively,the" with --alternatively, the--

At column 8, line 14:

Replace "disposing step" with --balloon blank--

Signed and Sealed this

Thirteenth Day of April, 2010

David J. Kappos
*Director of the United States Patent and Trademark Office*